United States Patent [19]
Karjalainen et al.

[11] Patent Number: 5,962,495
[45] Date of Patent: Oct. 5, 1999

[54] SELECTIVE AROMATASE INHIBITING COMPOUNDS

[75] Inventors: Arto Johannes Karjalainen; Marja-Liisa Södervall; Arja Marketta Kalapudas; Reino Olavi Pelkonen, all of Oulu; Aire Marja Laine, Turku; Risto Arvo Sakari Lammintausta, Turku; Jarmo Sakari Salonen, Turku, all of Finland

[73] Assignee: Risto Arvo Sakari Lammintausta, Turku, Finland

[21] Appl. No.: 08/929,424

[22] Filed: Sep. 15, 1997

Related U.S. Application Data

[62] Division of application No. 08/436,389, filed as application No. PCT/FI93/00539, Dec. 14, 1993, Pat. No. 5,703,109.

[30] Foreign Application Priority Data

Dec. 16, 1992 [GB] United Kingdom .................... 9226209

[51] Int. Cl.[6] ........................ A61K 31/415; C07D 233/61
[52] U.S. Cl. ........................................ 514/399; 548/336.1
[58] Field of Search .......................... 548/336.1; 514/399

[56] References Cited

U.S. PATENT DOCUMENTS

| | | | |
|---|---|---|---|
| 4,749,713 | 6/1988 | Bowman et al. | 514/341 |
| 4,937,250 | 6/1990 | Bowman et al. | 514/341 |
| 4,978,672 | 12/1990 | Bowman et al. | 514/383 |
| 5,071,861 | 12/1991 | Bowman et al. | 514/332 |
| 5,073,574 | 12/1991 | Lang | 514/381 |
| 5,112,845 | 5/1992 | Bowman et al. | 514/399 |
| 5,344,834 | 9/1994 | Strehlke et al. | 514/317 |

FOREIGN PATENT DOCUMENTS

| | | |
|---|---|---|
| 0 236 940 A2 | 9/1987 | European Pat. Off. . |
| 0 390 558 A1 | 10/1990 | European Pat. Off. . |
| 0 408 509 A2 | 1/1991 | European Pat. Off. . |
| 1 580 535 | 12/1980 | United Kingdom . |
| WO 92/10482 | 6/1992 | WIPO . |
| WO 92/22537 | 12/1992 | WIPO . |

OTHER PUBLICATIONS

Cram and Hammond, 2nd ed., "Organic Chemistry," pp. 565–567 (1964).

Wiley et al., "Conjugate Addition Reactions of Azoles: 1,2,3–Triazole and Benzotriazole," *American Chem. Society* 76:4933–4935 (1954).

Wiley et al., "Conjugate Addition Reactions of Azoles. II. 1,2,4–Triazole, Tetrazole, Nitropyrazoles and Bentriazole," *American Chem. Society* 77:2572–2573 (1955).

Hanukoglu and Jefcoate, "Pregnenolone Separation from Cholesterol using Sephadex LH–20 Minicolumns," *Journal of Chromatography* 190:256–262 (1980).

Pasanen and Pelkonen, "Cholesterol Side–Chain Cleavage Activity in Human Placenta and Bovine Adrenals: An One–Step Method for Separation of Pregnenolone Formed In Vitro," *Steroids* 43(5):517–527 (1984).

Pasanen, "Human Placental Aromatase Activity: Use of a $C_{18}$ Reversed–Phase Cartridge for Separation of Tritiated Water or steroid Metabolites in Placentas from both Smoking and Non–Smoking Mothers In Vitro," *Biological Research in Pregnancy* 6(2):94–99 (1985).

Lipton et al., "Aromatase Activity in Primary and Metatastic Human Breast Cancer," *Cancer* 59(4):779–782 (1987).

*Primary Examiner*—Patricia L. Morris
*Attorney, Agent, or Firm*—Finnegan, Henderson, Farabow, Garrett & Dunner, L.L.P.

[57] ABSTRACT

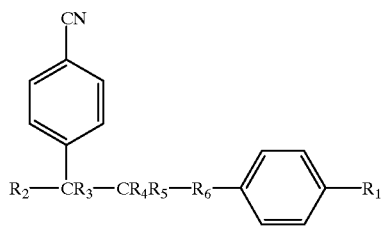

(I)

New compounds of formula (I) wherein $R_1$ is H, $CH_3$, $OCH_3$, $NO_2$, $NH_2$, CN, $CF_3$, $CHF_2$, $CH_2F$ or halogen, $R_2$ is a heterocyclyl radical selected from 1-imidazolyl, triazolyl, tetrazolyl, pyrazolyl, pyrimidinyl, oxazolyl, thiazolyl, isoxazolyl and isothiazolyl, $R_3$ is H or OH, $R_4$ is H, $R_5$ is H or OH; or $R_4$ is H and $R_3$ and $R_5$ combined form a bond; or $R_3$ is H and $R_4$ and $R_5$ combined form =O; $R_6$ is methylene, ethylene, —CHOH—, —$CH_2$—CHOH—, —CHOH—$CH_2$—, —CH=CH— or —C(=O)—; or $R_4$ is H and $R_5$ and $R_6$ combined is =CH— or =CH—$CH_2$—; stereoisomers thereof and non-toxic pharmaceutically acceptable acid addition salts thereof exhibit selective aromatase inhibiting properties, compared with their desmolase inhibiting properties. The compounds of the invention are valuable in the treatment of estrogen dependent diseases, e.g. breast cancer or benign prostatic hyperplasia (BPH).

10 Claims, No Drawings

SELECTIVE AROMATASE INHIBITING COMPOUNDS

This is a division of application Ser. No. 08/436,389, filed May 19, 1995, now U.S. Pat. No. 5,703,109, issued Dec. 30, 1997 which is a § 371 application of PCT/FI93/00539, filed Dec. 14, 1993.

The present invention relates to novel heterocyclic diarylalkyl compounds, their stereoisomers and their non-toxic, pharmaceutically acceptable acid addition salts, and their preparation, to pharmaceutical compositions containing the same and their use.

The compounds of the present invention have the general formula (I):

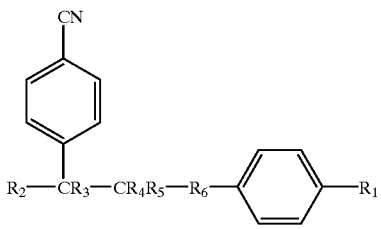

(I)

wherein $R_1$ is H, $CH_3$, $OCH_3$, $NO_2$, $NH_2$, CN, $CF_3$, $CHF_2$, $CH_2F$ or halogen, $R_2$ is a heterocyclyl radical selected from 1-imidazolyl, triazolyl, especially 1-1,2,4-triazolyl, tetrazolyl, pyrazolyl, pyrimidinyl, oxazolyl, thiazolyl, isoxazolyl and isothiazolyl, $R_3$ is H or OH, $R_4$ is H, $R_5$ is H or OH; or $R_4$ is H and $R_3$ and $R_5$ combined form a bond; or $R_3$ is H and $R_4$ and $R_5$ combined form =O; $R_6$ is methylene, ethylene, —CHOH—, —CH$_2$—CHOH—, —CHOH—CH$_2$—, —CH=CH— or —C(=O)—; or $R_4$ is H and $R_5$ and $R_6$ combined is =CH— or =CH—CH$_2$—; stereoisomers thereof and non-toxic pharmaceutically acceptable acid addition salts thereof.

The compounds of formula (I) and their stereoisomers form acid addition salts with both organic and inorganic acids. They can thus form many pharmaceutically usable acid addition salts, as for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least one compound of formula (I), a stereoisomer or a non-toxic, pharmaceutically acceptable salt thereof, and a compatible pharmaceutically acceptable carrier therefor. EP-A-0390558 describes diphenyl substituted 4(5)-imidazolyl derivatives which are disclosed to be aromatase inhibitors. U.S. Pat. No. 4,978,672 describes diphenyl substituted 1-1,2,4- and 1-1,3,4-triazolyl derivatives wherein the carbon chain between the phenyl groups is preferably methyl, such as 2-[alpha-(4-chlorophenyl)-1-(1, 2,4-triazolyl)methyl]benzonitrile. U.S. Pat. No. 4,937,250 describes diphenyl substituted 1-imidazolyl derivatives, U.S. Pat. No. 5,071,861 describes diphenyl substituted 3-pyridyl derivatives and U.S. Pat. No. 5,073,574 describes diphenyl substituted 1- and 2-tetrazolyl derivatives. The derivatives of the above mentioned U.S. patents are also stated to be aromatase inhibitors.

The compounds of the present invention have selective aromatase inhibiting properties, compared with their desmolase inhibiting properties. They are therefor valuable in the treatment of estrogen dependent diseases, e.g. breast cancer or benign prostatic hyperplasia (BPH). The selectivity of the compounds of formula (I) is regulated by the stereochemical isomerism.

The absolute stereochemical configuration of the compounds of formula (I) is not experimentally determined. It is conventionally agreed to designate the stereoisomers as "a", "b" and so on, without further reference to the absolute stereochemical configuration.

Stereoisomers of the compounds of formula (I) are naturally intended to be embraced within the scope of the invention.

Compounds of formula (I) can be prepared by reacting a halogenide of the formula (II)

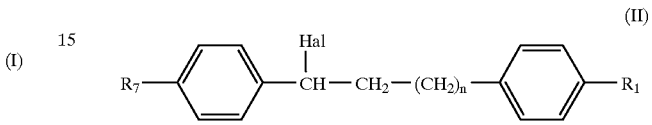

(II)

wherein Hal is a halogen, preferably bromide or chloride, n is 1 or 2, $R_1$ is as described before and $R_7$ is CN or other functional group which may be converted to cyano group by methods that are common in preparative organic chemistry, with a heterocyclic compound $R_2$'H wherein $R_2$' is 1-imidazolyl, 1-1,2,4-, 4-1,2,4-, 1-1,2,3- or 2-1,2,3-triazolyl or 1- or 2-tetrazolyl, in an appropriate solvent to give compounds of formula (III).

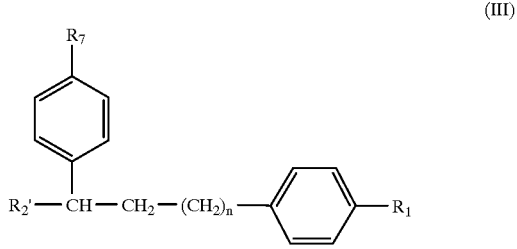

(III)

The heterocyclic compound is preferably in the form of its salt, preferably sodium salt. The starting compounds (II) can be prepared by conventional methods from an optionally substituted benzaldehyde and an appropriate benzene derivative.

The corresponding compounds of formula (III) wherein the $R_2$' is 4-1,2,3-, 3-1,2,4-triazolyl or 5-tetrazolyl may be prepared by the method described above in the presence of a strong base, such as an alkyl lithium, when the heterocyclic starting compound is N-protected by a suitable protecting group.

Compounds of formula (I) can also be prepared by allowing a derivative of the formula (IV)

(IV)

wherein $R_2$ and $R_7$ are as described above and $R_2$ is optionally protected by conventional methods, to react with an appropriate halogenide of the formula (V)

(V)

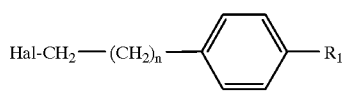

wherein Hal is halogen, preferably bromide or chloride, n is 1 or 2 and $R_1$ is as described above, in the presence of a strong base, such as an alkyl lithium, preferably n-butyl lithium, to give compounds of formula (III) wherein $R_2'$ is $R_2$.

Another method is to allow a compound of formula (IV) to react with an appropriate aldehyde of the formula (VI)

(VI)

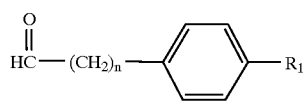

wherein n and $R_1$ are as described above, in the presence of a strong base, such as an alkyl lithium, preferably n-butyl lithium, to give compounds of formula (VII)

(VII)

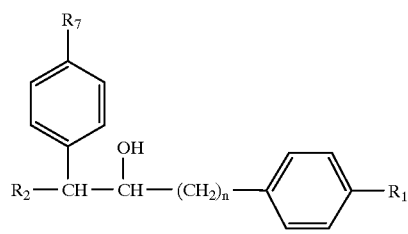

which may further be dehydrated by conventional methods such as refluxing with $SOCl_2$, $POCl_3$ or $PCl_5$ optionally in an appropriate solvent, such as acetonitrile, to give compounds of formula (VIII).

(VIII)

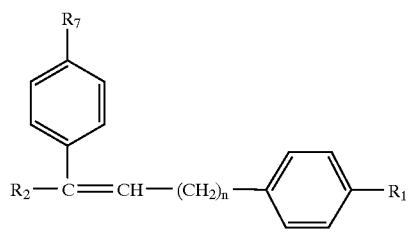

Compounds of formula (VIII) may further be catalytically hydrogenated if desired to give the corresponding saturated compounds.

Another method to get compounds of formula (I) is to allow compounds of formula (IV) wherein $R_2$ and $R_7$ are as defined before to react with an appropriate ester of formula (IX)

(IX)

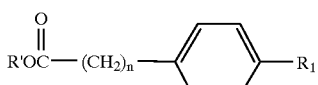

wherein R' is lower alkyl, preferably methyl or ethyl, in the presence of a strong base, such as an alkyl lithium, preferably n-butyl lithium, to give compounds of formula (X)

(X)

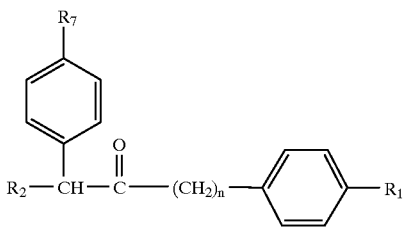

which is further reduced by common methods, e.g. with $NaBH_4$, to give the corresponding alcohols of formula (VII).

Compounds of formula (I) can also be prepared by reacting a heterocyclic compound $R_2'H$ wherein $R_2'$ is as defined before with a ketone of formula (XI)

(XI)

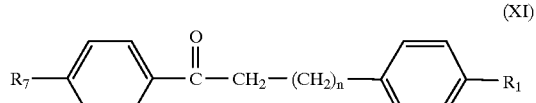

in the presence of thionyl chloride to give unsaturated compounds of formula (VIII) wherein $R_2$ is $R_2'$. The starting compounds of formula (XI) can be prepared by conventional methods from an optionally substituted benzaldehyde and an appropriate benzene derivative.

Compounds of formula (I) can be prepared by reacting a ketone of formula (XII)

(XII)

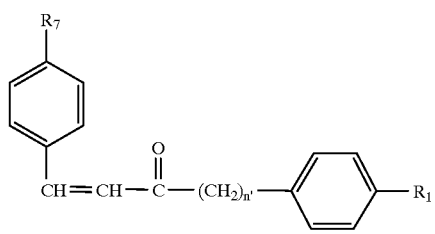

wherein $R_1$ and $R_7$ are as defined before and n' is 0 or 1, with a heterocyclic compound $R_2'H$ wherein $R_2'$ is as defined before by the method described in J. Am. Chem. Soc. Vol 77 (1955) p. 2572 and Vol 76 (1954) p. 4933 to give ketones of formula (XIII)

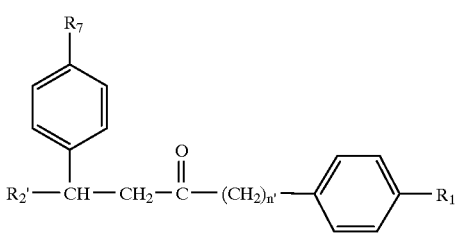
(XIII)

wherein R₂' is as described above, which are further reduced to give compounds of formula (XIV)

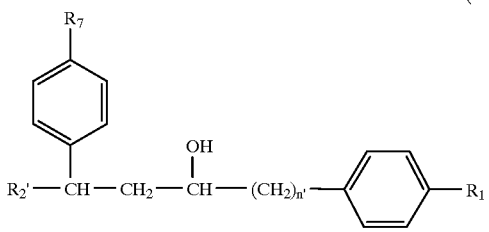
(XIV)

which may be dehydrated if desired to give unsaturated compounds of formula (I).

Yet another method for the preparation of compounds of formula (I) comprises a reaction of a compound of formula (IV) with a formamide in the presence of a strong base, such as n-butyl lithium, to give compounds of formula (XV).

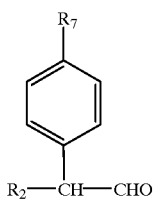
(XV)

An aldol condensation of the compounds of formula (XV) with an appropriate acetophenone produces unsaturated ketones which may be further reduced to alcohols included in the formula (I).

Compounds of formula (VIII) may also be prepared by allowing a ketone of formula (XVI)

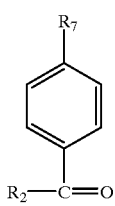
(XVI)

wherein $R_2$ and $R_7$ are as defined before and $R_2$ is optionally protected, to react with compounds of formulae (XVII) or (XVIII)

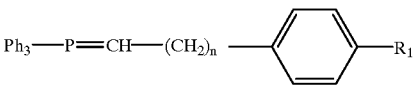
(XVII)

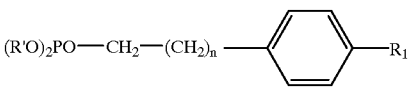
(XVIII)

wherein R' is lower alkyl, n is 1 or 2 and $R_1$ is as described before, in an inert solvent, for example tetrahydrofuran, according to WO92/10482.

Compounds of formula (I) wherein $R_3$ is OH can be prepared by reacting a compound of formula (XIX)

$$R_2'—Y \quad (XIX)$$

wherein R₂' is 4-1,2,3- or 3-1,2,4-triazolyl, 5-tetrazolyl, 3- or 4-pyrazolyl, 2-, 4- or 5-pyrimidinyl, 2-, 4- or 5-oxazolyl, 2-, 4- or 5-thiazolyl, 3-, 4- or 5-isoxazolyl or 3-, 4- or 5-isothiazolyl and Y is H or a protecting group, with a ketone of formula (XI) in the presence of strong base, such as an alkyl lithium, e.g. n-butyl lithium, to give compounds of formula (XX)

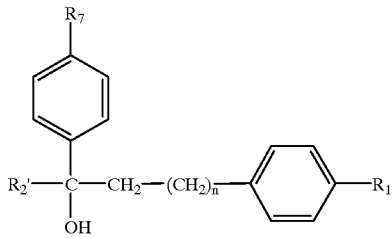
(XX)

which may further be dehydrated and hydrogenated if desired.

Compounds of formula (XX) may also be prepared by allowing a ketone of formula (XVI) to react with a halogenide of formula (V). The reaction is carried out in an appropriate solvent, such as tetrahydrofuran, in the presence of an alkyl lithium, e.g. n-butyl lithium, or magnesium.

Compounds of formula (XIV) wherein R₂' is R₂ may be prepared by reacting an epoxide derivative of formula (XXI)

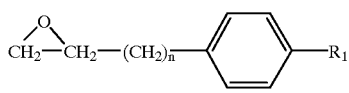
(XXI)

wherein $R_1$ is as defined before and n' is 0 or 1, with compounds of formula (IV) in the presence of strong base.

$R_7$ which may be converted to cyano is for example nitro, amino, halogen, preferably bromide, formyl or carboxylic acid amide.

Compounds of formulae (III), (VII), (VIII), (X), (XIII), (XIV), (XV) and (XX) wherein $R_7$ is nitro can be converted to compounds of formula (I) by hydrogenation and further diazotization of the amino group.

Compounds of formulae (III), (VII), (VIII), (X), (XIII), (XIV), (XV) and (XX) wherein $R_7$ is halogen can be converted to compounds of formula (I) by using e.g. a cyanide salt, especially sodium or potassium cyanide.

Compounds of formulae (III), (VII), (VIII), (X), (XIII), (XIV), (XV) and (XX) wherein $R_7$ is formyl can be converted to compounds of formula (I) by methods described in the literature.

Compounds of formulae (III), (VII), (VIII), (X), (XIII), (XIV), (XV) and (XX) wherein $R_7$ is a carboxylic acid amide can be converted to compounds of formula (I) by reacting refluxing with e.g. $SOCl_2$ or $PCl_5$.

In starting compounds and intermediates which are converted to the compounds of the invention by the reactions described above, functional groups present, such as $NH_2$, CN and ring NH, are optionally protected by conventional methods that are common in preparative organic chemistry to protect the functional groups from undesired reactions.

Protecting groups for the nitrogen in the heterocyclyl radicals are preferably tri-lower alkyl silyl, such as trimethylsilyl.

Stereoisomers of the compounds of formula (I) may be obtained by the application of art-known separation methods such as selective crystallization and chromatographic techniques, such as column chromatography and high performance liquid chromatography.

The compounds of formula (I), their non-toxic, pharmaceutically acceptable acid addition salts or mixtures thereof may be administered parenterally, intravenously or orally. Typically, an effective amount of the compound is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the compound is administer, etc., and of course the structure of the compound.

The pharmaceutical carriers which are typically employed with the compounds of the present invention may be solid or liquid and are generally selected with the planned manner of administration in mind. Thus, for example, solid carriers include lactose, sucrose, gelatin and agar, while liquid carriers include water, syrup, peanut oil and olive oil. Other combinations of the compound and the carrier may be fashioned into numerous acceptable forms, such as tablets, capsules, suppositories, solutions, emulsions and powders.

The compounds of the invention are especially valuable as aromatase inhibiting agents and are therefore useful in the treatment of estrogen dependent diseases, e.g. breast cancer or benign prostatic hyperplasia (BPH).

Estrogens are essential steroids in the physiology and function of normal development of breast and sex organs in women. On the other hand estrogens are known to stimulate the growth of estrogen dependent cancers, especially breast and endometrial cancers, and they may increase the risk of development of breast cancer if given at pharmacological doses for a long time. Excessive production of estradiol may also cause other, benign disorders in hormone dependent organs. The importance of estrogens as cancer growth stimulators and/or regulators is clearly stressed by the fact that antiestrogens have reached a central position in the treatment of estrogen receptor rich breast cancers. Antiestrogens act by binding to estrogen receptors and thereby inhibiting the biological effect of estrogens. This has been achieved clinically by the unspecific steroid synthesis inhibitor aminoglutethimide. The estrogen synthesis could be blocked specifically by inhibiting the enzyme aromatase, which is the key enzyme in biochemical estrogen synthesis pathway. Aromatase inhibition is important because several breast mmors synthesize estradiol and estrone in situ and exhibit therefore continuous growth stimulation (Alan Lipton et al., Cancer 59:770–782, 1987).

The ability of the compounds of the invention to inhibit the enzyme aromatase was shown by the in vitro assay method according to M. Pasanen (Biological Research in Pregnancy, vol. 6, No. 2, 1985, pp. 94–99). Human aromatase enzyme was used. The enzyme was prepared from human placenta, which is rich of the enzyme. Microsomal fraction (100000×g precipitate) was prepared by centrifugation. The enzyme preparation was used without further purification. Test compounds listed in Table 1 were added together with 100000 dpm of $1,2[^3H]$-androstene-3,17-dione and NADPH generating system. The concentrations of the test compounds were 0.001; 0.01; 0.1 and 1.0 mM. The incubation was carried out at 37° C. for 40 min. Aromatization of $1,2[^3H]$-androstene-3,17-dione results in the production of $^3H_2O$. The tritiated water and the tritiated substrate are easily separated by a Sep-Pak$^R$ minicolumn, which absorbs the steroid but allows free water elution. Radioactivity was counted by a liquid scintillation counter. Aromatase inhibition was evaluated by comparing the $^3H_2O$-radioactivity of inhibitor treated samples to controls containing no inhibitor. IC-50 values were calculated as concentrations which inhibited the enzyme activity 50%. These concentrations are presented in Table 2.

Cholesterol side chain cleavage (SCC) activity (desmolase) was measured according to the method of Pasanen and Pelkonen (Steroids 43:517–527, 1984). Incubations were carried out in 1,5 ml Eppendorf plastic tubes, and an Eppendorf shaker, centrifuge and incubator were used as a unit In a 300 µl incubation volume, the substrate (5 µM) was prepared according to Hanukoglu and Jefcoate (J. Chromatogr. 190:256–262, 1980), and 100000 dpm of radioactive $^3H$-4cholesterol (the purity of the compound was checked by TLC) in 0.5% Tween 20, 10 mM $MgCl_2$, 5 µM cyanoketone and 2 mM NADPH was added. Controls contained all the above substances but the enzyme preparation was inactivated prior to the incubation by the addition of 900 µl of methanol. The mitochondrial fraction (1 mg protein) from human placenta or bovine adrenals was used as a source of enzyme. After 30 min incubation at 37° C., the reaction was terminated by the addition of 900 µl of methanol; 1500 dpm of marker $^{14}C$-4-pregnenolone was added to each incubate and the tubes were vigorously shaken. After 10 min equilibration, the methanol-precipitated proteins were separated by centrifugation (8000×g for 2 min) and the supernatant was sucked into 1 ml plastic injection syringe and loaded onto the pre-equilibrated (75% methanol) minicolumn. The column was washed with one ml of 75% methanol and then with 3 ml of 80% methanol. The 80% methanol eluate was run into the counting vial and 10 ml of scintillation liquid was added Radioactivity was counted using a double-label program on a liquid scintillation counter (LKB RackBeta). Typical activities for placental and bovine adrenal enzyme preparation were 0.5–3 and 50–100 pmol pregnenolone formed/mg proteinmnin, respectively.

In inhibition experiments, the substance (final concentration range from 1 to 1000 µM) was added into incubation mixture in a volume of 10–20 µl, usually as methanol or ethanol solution. The same volume of the solute was added into control incubation vial. The IC-50 values (concentration causing a 50% inhibition) were determined graphically and are presented in Table 2.

TABLE 1

Compounds tested

| No. | Name |
|-----|------|
| 1. | 1-[1-(4-cyanophenyl)-4-(4-fluorophenyl)butyl]-1H-imidazole |
| 2. | 1-[1-(4-cyanophenyl)-4-(4-fluorophenyl)-2-hydroxybutyl]-1H-imidazole, diastereomer a + d |
| 3. | 1-[1-(4-cyanophenyl)-4-(4-fluorophenyl)-1-butenyl]-1,2,4-triazole, isomer b |
| 4. | 1-[1-(4-cyanophenyl)-3-(4-fluorophenyl)-2-hydroxypropyl]-1,2,4-triazole, diastereomer a + d |
| 5. | 1-[1-(4-cyanophenyl)-4-(4-fluorophenyl)-2-hydroxybutyl]-1,2,4-triazole, diastereomer a + d |
| 6. | 1-[1-(4-cyanophenyl)-3-(4-fluorophenyl)-3-hydroxypropyl]-1,2,4-triazole |
| 7. | 1-[1-(4-cyanophenyl)-4-(4-fluorophenyl)-2-oxobutyl]-1,2,4-triazole |
| 8. | 1-[1-(4-cyanophenyl)-3-(4-fluorophenyl)-1-propenyl]-1,2,4-triazole, isomer b |
| 9. | 5-[1-(4-cyanophenyl)-3-(4-fluorophenyl)-1-hydroxypropyl]thiazole |

TABLE 2

Inhibition of human aromatase and desmolase by test compounds IC-50 represents the concentration which inhibits the enzyme 50%

| Compound No. | AROMATASE IC-50 µmol/l | DESMOLASE IC-50 µmol/l |
|---|---|---|
| 1. | 0.042 | 17.0 |
| 2. | 0.180 | 49.0 |
| 3. | 0.140 | 300 |
| 4. | 0.260 | >1000 |
| 5. | 0.950 | >1000 |
| 6. | 0.300 | 380 |
| 7. | 0.900 | 172 |
| 8. | 0.052 | 165 |
| 9. | 0.280 | 300 |

In general the daily dose for a patient would be from about 10 to about 200 mg, administered orally.

Acute toxicity, $LD_{50}$, of 1-[1-(4-cyanophenyl)-3-(4-fluorophenyl)-2-hydroxypropyl]-1,2,4-triazole diastereomer a+d was determined by using young adult female mice of NMRI-strain. The administration of the test compound was oral. The highest dose tested was 400 mg/kg and it was well tolerated. No adverse effects were seen.

The following examples illustrate the invention.

$^1$H NMR spectra were determined with a Bruker AC-300 P apparatus. The reference substance was tetramethylsilane.

EXAMPLE 1

1-[1-(4-cyanophenyl)-4-(4-fluorophenyl)butyl]-1H-imidazole 1-(4-cyanobenzyl)-imidazole (1 g, 0.0054 mol) is dissolved into dry tetrahydrofuran (30 ml) and cooled to −70° C. n-BuLi in hexane (0.0054 mol) is added dropwise into the reaction mixture. After stirring for additional 30 min at −70° C. 3-(4-fluorophenyl)propyl bromide (1.5 g, 0.0069 mol) in THF (10 ml) is added to the mixture and stirig is continued for 2 hours. Then the mixture is allowed to warm to room temperature. Saturated aqueous ammonium chloride solution is added to the mixture, shaked and then the layers are separated. THF-phase is dried and evaporated to dryness. The residue is crystalizd from isopropanol as hydrogen chloride salt. The filtrate is purified by flash chromatography.

$^1$H NMR (HCl-salt, MeOH-$d_4$): 1.5–1.63 (quintet, 2H), 2.3–2.5 (m, 2H), 2.7 (t, 2H), 5.75 (t, 1H), 6.94–7.00 (m, 2H), 7.14–7.19 (m, 2H), 7.62 (d, 2H), 7.63 (s, 1H), 7.78 (s, 1H), 7.8 (d, 2H), 9.6 (s, 1H)

EXAMPLE 2

1-[1-(4-cyanophenyl)-4-(4-fluorophenyl)butyl]-1,2,4-triazole

The compound is prepared by the method described in Example 1 starting from 1-(4-cyanobenzyl)-1,2,4-triazole (6.0 g, 0.0272 mol), n-BuLi (0.0272 mol) and 3-(4-fluorophenyl)propylbromide (7.6 g, 0.035 mol). The product is purified first by suspending the residue with 2 M aqueous hydrogen chloride and petrol ether. Petrol ether phase is separated and the aqueous layer and the separated oil are extracted with diethyl ether. Diethyl ether phase is evaporated and the residue is purified by flash chromatography.

$^1$H NMR (HCl-salt, CDCl$_3$): 1.4–1.65 (m, 2H), 2.2–2.4 (m, 1H), 2.45–2.6 (m, 1H), 2.67 (t, 2H), 6.12 (t, 1H), 6.94 (t, 2H), 7.06–7.10 (m, 2H), 7.67 (d, 2H), 7.73 (d, 2H), 8.43 (s, 1H), 11.31 (s, 1H)

EXAMPLE 3

1-[1-(4-cyanophenyl)-4-phenyl-1-butenyl]-1,2,4-triazole a) 1-[1-(4-cyanophenyl)-2-hydroxy-4-phenylbutyl]-1,2,4-triazole 1-[1-(4-cyanophenyl)-2-hydroxy-4-phenylbutyl]-1,2,4-triazole is prepared by the method described in Example 1 starting from 1-(4-cyanobenzyl)-1,2,4-triazole (2.0 g, 0.0108 mol), n-BuLi (0.0108 mol) and 3-phenylpropionaldehyde (1.74 g, 0.013 mol). The product is purified by flash chromatography.

$^1$H NMR (base, CDCl$_3$): 1.5–1.75 (m, 2H), 2.6–2.75 (m, 1H), 2.8–2.95 (m, 1H), 4.3–4.5 (m, 1H), 5.25–5.27 (m, 1H), 7.0–7.35 (m, 5H), 7.39 and 7.51 (d, 2H), 7.60 (d, 2H), 7.89 and 7.91 (s, 1H), 8.08 and 8.13 (s, 1H)

The following compounds included in the invention were prepared by the same procedure:

1-[1-(4-cyanophenyl)-4-(4-fluorophenyl)-2-hydroxybutyl]-1,2,4-triazole, diastereomers a+d and b+c $^1$H NMR (base, CDCl$_3$):

diastereomer a+d: 1.5–1.7 (m, 2H), 2.6–2.73 (m, 1H), 2.8–2.9 (m, 1H), 4.4–4.5 (m, 1H), 5.23 (d, 1H), 6.96 (t, 2H), 7.11 (dd, 2H), 7.48 (d, 2H), 7.66 (d, 2H), 8.05 (s, 1H), 8.08 (s,1H)

diastercomer b+c: 1.5–1.7 (m, 2H), 2.63–2.73 (m, 1H), 2.8–2.9 (m, 1H), 4.3–4.4 (m, 1H), 5.26 (d, 1H), 6.95 (t, 2H), 7.05 (dd, 2H), 7.38 (d, 2H), 7.65 (d, 2H), 8.07 (s, 1H), 8.12 (s, 1H)

1-[1-(4-cyanophenyl)-4-(4-fluorophenyl)-2-hydroxybutyl]-1H-imidazole, diastereomers a+d and b+c diastereomer a+d:

$^1$H NMR (base, CDCl$_3$): 1.6–1.8 (m, 2H), 2.6–2.75 (m, 1H), 2.81–2.9 (m, 1H), 4.24–4.3 (m, 1H), 5.04 (d, 1H), 6.9–7.0 (m, 4H), 7.08–7.12 (m, 2H), 7.49 (d, 2H), 7.57 (s, 1H), 7.67 (d, 2H)

diastereomer b+c:

$^1$H NMR (base, CDCl$_3$+MeOH-$d_4$): 1.6–1.8 (m, 2H), 2.6–2.73 (m, 1H), 2.8–2.89 (m, 1H), 4.21–4.27 (m, 1H), 5.09 (d, 1H), 6.93–7.11 (m, 6H), 7.3 (d, 2H), 7.64 (d, 2H), 7.69 (s, 1H)

b) 1-[1-(4-cyanophenyl)-4-phenyl-1-butenyl]-1,2,4-triazole

1-[1-(4-cyanophenyl)-2-hydroxy4-phenylbutyl]-1,2,4-triazole (0.42 g, 0.00132 mol) is dissolved into acetonitrile.

Phosphorous pentachloride (0.27 g, 0.0013 mol) is added into the solution and the mixture is refluxed for 2 hours. Acetonitrile is evaporated, the residue is dissolved with 2 M aqueous sodium hydroxide and extracted with methylene chloride. Methylene chloride is dried and the product is crystallized from ethyl acetate as hydrogen chloride salt (isomer a).

$^1$H NMR (HCl-salt, MeOH-d$_4$): 2.40 (q, 2H), 2.85 (t, 2H), 6.82 (t, 1H), 6.84–7.28 (m, 5H), 7.32 (d, 2H), 7.72 (d, 2H), 8.58 (s, 1H), 8.65 (s, 1H)

The following compounds included in the invention were prepared by the same procedure:

1-[1-(4-cyanophenyl)-4-(4-fluorophenyl)-1-butenyl]-1,2,4-triazole, isomers a and b $^1$H NMR (HCl-salt, MeOH-d$_4$):

isomer a: 2.42 (q, 2H), 2.85 (t, 2H), 6.85 (t, 1H), 7.0 (t, 2H), 7.16–7.21 (m, 2H), 7.37 (d, 2H), 7.74 (d, 2H), 8.82 (s, 1H), 9.38 (s, 1H)

isomer b: 2.53 (q, 2H), 2.83 (t, 2H), 6.63 (t, 1H), 6.98 (t, 2H), 7.12–7.17 (m, 2H), 7.33 (d, 2H), 7.80 (d, 2H), 8.62 (s, 1H), 9.33 (s, 1H)

1-[1-(4-cyanophenyl)-4-(4-fluorophenyl)-1-butenyl]-1H-imidazole, isomers a and b isomer a: $^1$H NMR (base, CDCl$_3$): 2.4 (q, 2H), 2.77 (t, 2H), 6.33 (t, 1H), 6.69 (s, 1H), 7.0 (t, 2H), 7.05–7.1 (m, 2H), 7.15 (d, 2H), 7.19 (s, 1H), 7.3 (s, 1H), 7.6 (d, 2H)

isomer b:
$^1$H NMR (HCl-salt, CDCl$_3$): 2.56 (q, 2H), 2.87 (t, 2H), 6.55 (t, 1H), 6.89 (s, 1H), 7.0 (t, 2H), 7.11 (dd, 2H), 7.19 (d, 2H), 7.44 (s, 1H), 7.72 (d, 2H), 9.64 (s, 1H)

EXAMPLE 4

1-[1-(4-cyanophenyl)-3-(4fluorophenyl)propyl]-1,2,4-triazole a) 1-(4-cyanophenyl)-3-(4-fluorophenyl)prop-2-en-1-one 4-Acetylbenzonitrile (14.5 g, 0.1 mol) and 4-fluorobenzaldehyde (12.1 g, 0.1 mol) are dissolved in methanol (150 ml) and solid sodium hydroxide is added to make the solution alkaline. The mixture is stirred in room temperature for 6 hours. The product is filtered off and washed with methanol.

$^1$H NMR (CDCl$_3$): 7.14 (t, 2H), 7.40 (d, 1H), 7.66 (dd, 2H), 7.81 (d, 1H), 7.82 (d, 2H), 8.09 (d, 2H)

b) 1-(4-cyanophenyl)-3-(4-fluorophenyl)-1-propanone 1-(4-cyanophenyl)-3-(4-fluorophenyl)prop-2-en-1-one is hydrogenated in ethanol using 5% Pd-C as a catalyst.

$^1$H NMR (CDCl$_3$): 3.05 (t, 2H), 3.29 (t, 2H), 6.98 (t, 2H), 7.20 (dd, 2H), 7.76 (d, 2H), 8.02 (d, 2H)

c) 1-(4-cyanophenyl)-3-(4-fluorophenyl)-1-propanol 1-(4-cyanophenyl)-3-(4-fluorophenyl)-1-propanone (6.35 g, 25 mmol) is dissolved in methanol (50 ml). Sodium borohydride (0.48 g, 12.6 mmol) is added and the mixture is stirred in 30° C. for 1 h. The mixture is rendered acidic with 2M hydrochloric acid and the solvent is evaporated. The residue is dissolved into ethyl acetate. The solution is washed with dilute sodium hydroxide and water, dried and the solvent is evaporated. The product is used for the next step without further purification.

$^1$H NMR (CDCl$_3$): 1.94–2.10 (m, 2H), 2.66–2.74 (m, 2H), 4.74 (dd, 1H), 6.97 (t, 2H), 7.13 (dd, 2H), 7.45 (d, 2H), 7.64 (d, 2H)

d) 1-chloro-1-(4-cyanophenyl)-3-(4-fluorophenyl)propane 1-(4-cyanophenyl)-3-(4-fluorophenyl)-1-propanol (3.43 g, 13 mmol) is dissolved in dichloromethane (20 ml). Thionylchloride (1.2 ml, 16 mmol) is added dropwise to the cooled solution and the mixture is stirred in room temperature for 2 hours. The mixture is washed with water, dried and the solvent is evaporated. The residue is used for the next step without further purification.

$^1$H NMR(CDCl$_3$): 2.20–2.44 (m, 2H), 2.66–2.83 (m, 2H), 4.77 (dd, 1H), 6.99 (t, 2H), 7.13 (dd, 2H), 7.46 (d, 2H), 7.65 (d, 2H)

e) 1-[1-(4-cyanophenyl)-3-(4-fluorophenyl)propyl]-1,2,4-triazole

The mixture of 1-chloro-1-(4-cyanophenyl)-3-(4-fluorophenyl)propane (4.18 g, 15 mmol) and 1,2,4-triazole sodium derivative (1.37 g, 15 mmol) in DMF (30 ml) is heated mildly for 4 h. DMF is evaporated The residue is dissolved in ethyl acetate and washed with water. The organic layer is dried and the solvent is evaporated. The product is purified with flash chromatography (Silica gel 60 mesh 230–400, eluent: methylene chloride-methanol 99:1).

$^1$H NMR (HCl-salt, MeOH-d$_4$): 2.55–2.65 (m, 3H), 2.78–2.84 (m, 1H), 5.83 (dd, 1H), 7.00 (t, 2H), 1.17 (dd, 2H), 7.68 (d, 2H), 6.78 (d, 2H), 8.75 (s, 1H), 9.69 (s, 1H)

1-[1-(4-cyanophenyl)-3-(4-fluorophenyl)propyl]-1H-imidazole is prepared according to the same procedure using 1-chloro-1-(4cyanophenyl)-3-(4-fluorophenyl)propane and 1H-imidazole sodium derivative as starting materials.

$^1$H NMR (HCl-salt, MeOH-d$_4$): 2.59–2.80 (m, 4H), 5.72 (m, 1H), 7.00 (t, 2H), 7.19 (dd, 2H), 7.63 (d, 2H), 7.67 (s, 1H), 7.81 (d, 2H), 7.84 (s, 1H), 9.23 (s, 1H)

EXAMPLE 5

1-[1-(4-cyanophenyl)-3-(4-fluorophenyl)propyl]-1H-imidazole

1-[1-(4-cyanophenyl)-3-(4-fluorophenyl)propyl]-1H-imidazole is prepared according to the procedure described in Example 1 using 4-fluorophenethyl bromide as an alkylating agent. The product is purified by flash chromatography.

$^1$H NMR (HCl-salt, MeOH-d$_4$): 2.59–2.80 (m, 4H), 5.72 (m, 1H), 7.00 (t, 2H), 7.19 (dd, 2H), 7.63 (d, 2H), 7.67 (s, 1H), 7.81 (d, 2H), 7.84 (s, 1H), 9.23 (s, 1H)

1-[1-(4-cyanophenyl)-3-(4-fluorophenyl)propyl]-1,2,4-triazole is prepared according to the same procedure using 1-(4cyanophenyl)-1,2,4-triazole and 4-fluorophenetyl bromide as starting materials. The product is purified by flash chromatography.

EXAMPLE 6

1-[1-(4-cyanophenyl)-3-(4-fluorophenyl)-1-propenyl]-1H-imidazole a) 1-[1-(4-cyanophenyl)-3-(4-fluorophenyl)-2-hydroxypropyl]-1H-imidazole 1-[1-(4-cyanophenyl)-3-(4-fluorophenyl)-2-hydroxypropyl]-1H-imidazole is prepared according to the procedure of Example 1 using 1-(4-cyanobenzyl)-imidazole and 4-fluorophenylacetaldehyde as starting materials. The product is purified by flash chromatography.

$^1$H NMR (HCl-salt, MeOH-d$_4$): 2.57–2.70 (m, 1H), 2.75–2.82 (m, 1H), 4.62–4.68 (m, 1H), 5.64–5.66 (m, 1H), 6.97–7.05 (m, 2H), 7.17–7.24 (m, 2H), 7.54–7.85 (m, 6H), 9.16 and 9.21 (2s, together 1H)

b) 1-[1-(4cyanophenyl)-3-(4-fluorophenyl)-1-propenyl]-1H-imidazole

1-[1-(4-cyanophenyl)-3-(4-fluorophenyl)-2-hydroxypropyl]-1H-inidazole is dehydrated according to the procedure of Example 3b. The product is a mixture of E- and Z-isomers (1:1). The product is purified by flash chromatography.

$^1$H NMR (base, CDCl$_3$): 3.42 and 3.52 (2d, together 2H), 6.16 and 6.50 (2t, together 1H), 6.91–7.12 (m, 6H), 7.26 and 7.42 (2d, together 2H), 7.55 and 7.59 (2s, together 1H), 7.62 and 7.75 (2d, together 2H)

EXAMPLE 7

1-[1-(4-cyanophenyl)-3-(4-fluorophenyl)-1-propenyl]-1H-imidazole

Imidazole (0.55 g, 8 mmol) is dissolved in dry tetrahydrofuran. The solution is cooled on icebath and $SOCl_2$ (0.16 ml, 2 mmol) is added dropwise to the cooled solution. The mixture is stirred for 10 min. 1-(4-cyanophenyl)-3-(4-fluorophenyl)-1-propanone (0.34 g, 1.3 mmol) is added and the mixture is stirred in room temperature for 4 days. Methylene chloride is added and tie mixture is washed with water. The organic layer is dried and the solvent is evaporated. The residue contains 35% of the product ($^1H$ NMR) as a 9:1 mixture of the isomers. The product is purified by flash chromatography (eluent $CH_2Cl_2$-MeOH 99:1).

isomer b: $^1H$ NMR (HCl-salt, MeOH-$d_4$): 3.62 (d, 2H), 6.65 (t, 1H), 7.05 (t, 2H), 7.26 (dd, 2H), 7.63 (d, 2H), 7.66 (s, 1H), 7.69 (s, 1H), 7.91 (d, 2H), 9.16 (s, 1H)

EXAMPLE 8

1-[1-(4-cyanophenyl)-3-(4-fluorophenyl)-2-propenyl]-1,2,4-triazole a) 3-(4cyanophenyl)-1-(4-fluorophenyl)prop-2-en-1-one 3-(4cyanophenyl)-1-(4-fluorophenyl)prop-2-en-1-one is prepared according to the procedure described in Example 4a using 4-cyanobenzaldehyde and 4-fluoroacetophenone as starting materials.

$^1H$ NMR ($CDCl_3$): 7.21 (t, 2H), 7.59 (d, 1H), 7.73 (s, 4H), 7.79 (d, 1H), 8.08 (dd, 2H)

b) 3-(4-cyanophenyl)-1-(4-fluorophenyl)-3-(1-triazolyl)propanone 3-(4-cyanophenyl)1-(4-fluorophenyl)prop-2-en-1-one (2.5 g, 10 mmol), 1,2,4-triazole (0.7 g, 10 mmol) and one drop of Triton B are heated to solution. The cooled mixture is diluted with ether and the product is filtered off. The product is used for the next step without further purification.

$^1H$ NMR ($CDCl_3$): 3.61 (dd, 1H), 4.37 (dd, 1H), 6.25 (dd, 1H), 7.15 (t, 2H), 7.55 (d, 2H), 7.68 (d, 2H), 7.95 (s, 1H), 7.99 (m, 2H), 8.23 (s, 1H)

c) 1-[1-(4-cyanophenyl)-3-(4-fluorophenyl)-3-hydroxypropyl]-1,2,4-triazole

1-[1-(4cyanophenyl)-3-(4-fluorophenyl)-3-hydroxypropyl]-1,2,4-triazole is prepared from 3-(4-cyanophenyl)-1-(4-fluomophenyl)-3-(1-triazolyl)propanone according to the procedure of Example 4c. The product is purified by flash chromatography as a mixture of diastereomers (a+d:b+c, 2:1).

$^1H$ NMR (base, $CDCl_3$): 2.27–2.37 and 2.54–2.63 (2m, together 1H), 2.7–2.88 (m, 1H), 4.26 and 4.41 (2dd, together 1H), 5.62 and 5.91 (2dd, together 1H), 7.03 and 7.04 (2t, together 2H), 7.22–7.31 (m, 2H), 7.50 and 7.55 (2d, together 2H), 7.65 and 7.69 (2d, together 2H), 7.94 and 8.04 (2s, together 1H), 8.05 and 8.22 (2s, together 1H)

The mixture of diastereomers is triturated with diethylether and filtered. The diastmomer a+d is enriched in the insoluble material (>90%) and the diastercomer b+c in the filtrate (>80%). Both diastereomers are further purified by recrystallization from toluene.

$^1H$ NMR (HCl-salt, MeOH-$d_4$):
diastereomer a+d: 2.67 (ddd, 1H), 2.84 (dd, 1H), 4.54 (dd, 1H), 6.13 (dd, 1H), 7.04 (t, 2H), 7.33 (dd, 2H), 7.77 (d, 2H), 7.81 (d, 2H), 8.79 (s, 1H), 9.86 (s, 1H)

diastereomer b+c: 2.43 (ddd, 1H), 2.94 (ddd, 1H), 4.33 (dd, 1H), 6.14 (dd, 1H), 7.05 (t, 2H), 7.34 (dd, 2H), 7.66 (d, 2H), 7.75 (d, 2H), 8.69 (s, 1H), 9.62 (s, 1H)

d) 1-[1-(4cyanophenyl)-3-(4-fluorophenyl)-2-propenyl]-1,2,4-triazole

1-[1-(4-cyanophenyl)-3-(4-fluorophenyl)-3-hydroxypropyl]-1,2,4-triazole (100 mg) is heated with potassium hydrogen sulfate (400 mg) on oil bath at 140° C. for 2 hours. Methanol is added and the inorganic material is filtered off. Methanol is evaporated to give the product as a mixture of cis and trans isomers.

$^1H$ NMR (base, $CDCl_3$): 6.22 (m, 1H), 6.56 (m) vinyl protons of cis isomer, 6.47 (d) and 6.81 (dd) vinyl protons of trans isomer, 6.09 and 7.12 (2t, together 2H), 7.29–7.34 (m, 2H), 7.36 and 7.49 (2d, together 2H), 7.69 and 8.02 (2d, together 2H), 8.03 and 8.02 (2s, together 1H), 8.26 and 8.12 (2s, together 1H)

EXAMPLE 9

1-[1-(4-cyanophenyl)-3-(4-fluorophenyl)-1-propenyl]-1,2,4-triazole a) 1-[1-(4-cyanophenyl)-3-(4-fluorophenyl)-2-hydroxypropyl]-1,2,4-triazole 1-[1-(4-cyanophenyl)-3-(4-fluorophenyl)-2-hydroxypropyl]-1,2,4-triazole is prepared according to the procedure of Example 2 using 1-(4cyanophenyl)-1,2,4-triazole and 4-fluorophenylacetaldehyde as starting materials. The diastereomers of the product are separated by flash chromatography (eluent: ethyl acetate/methanol 95:5).

$^1H$ NMR (HCl-salt, MeOH-$d_4$):
diastereomer a+d: 2.62 (dd, 1H), 2.72 (dd, 1H), 4.73 (ddd, 1H), 5.73 (d, 1H), 7.00 (t, 2H), 7.19 (dd, 2H), 7.80 (s, 4H), 8.75 (s, 1H), 9.67 (s, 1H)

diastereomer b+c: 2.66–2.70 (m, 2H), 4.67 (dt, 1H), 5.70 (d, 1H), 6.98 (t, 2H), 7.15 (dd, 2H), 7.80 (m, 4H), 8.78 (s, 1H), 9.78 (s, 1H)

b) 1-[1-(4-cyanophenyl)-3-(4-fluorophenyl)-1-propenyl]-1,2,4-triazole

1-[1-(4-cyanophenyl)-3-(4-fluorophenyl)1-propenyl]-1,2,4-triazole is prepared according to the procedure of Example 3b from diastereomer b+c of 1-[1-(4-cyanophenyl)-3-(4-fluorophenyl)-2-hydroxypropyl]-1,2,4-tiazole. Mainly isomer a is produced by the procedure. The products are purified by flash chromatography.

$^1H$ NMR (HCl-salt of isomer a, MeOH-$d_4$): 3.47 (d, 2H), 6.97 (t, 1H), 7.04 (t, 2H), 7.26 (dd, 2H), 7.43 (d, 2H), 7.75 (d, 2H), 8.86 (s, 1H), 9.71 (s, 1H)

$^1H$ NMR (HCl-salt of isomer b, MeOH-$d_4$): 3.58 (d, 2H), 6.79 (t, 1H), 7.04 (t, 2H), 7.23 (d, 2H), 7.62 (d, 2H), 7.90 (d, 2H), 8.62 (s, 1H), 9.39 (s, 1H)

EXAMPLE 10

1-[1-(4-cyanophenyl)-4-(4-fluorophenyl)-2-oxobutyl]-1,2,4-triazole

1-[1-(4-cyanophenyl)-4-(4-fluorophenyl)-2-oxobutyl]-1,2,4-triazole is prepared according to the procedure described in Example 1 starting from 1-(4-cyanobenzyl)-1,2,4-triazole (1.7 g, 0.0092 mol), n-BuLi (0.0108 mol) and ethyl 3-(4-fluorophenyl)propionate (2.3 g, 0.0117 mol) prepared from 4-fluorocinnamic acid by esterification and hydrogenation. The product is purified by flash chromatography methylene chloride-methanol (95:5) as eluent.

$^1H$ NMR (base, $CDCl_3$): 2.65–2.95 (m, 4H), 6.15 (s, 1H), 6.93 (t, 2H), 7.04 (dd, 2H), 7.37 (d, 2H), 7.67 (d, 2H), 7.97 (s, 1H), 8.18 (s, 1H)

EXAMPLE 11

2-[1-(4-cyanophenyl)-3-(4-fluorophenyl)propyl]tetrzaole and 1-[1-(4-cyanophenyl)-3-(4-fluorophenyl)propyl]tetrzaole NaH (0.45 g of 55% suspension in mineral oil) is added to anhydrous DMF under nitrogen atmosphere. Tetrazole (1.1 g) is added and the mixture is gently heated for 20 minutes. The mixture is cooled to room temperature and 1-chloro-1-(4-cyanophenyl)3-(4-fluorophenyl)propane (1.53 g) is added. The reaction mixture is then heated for 6 hours. Water is added and the products are extracted into ethyl acetate. After drying and solvent evaporation the products are purified by flash chromatography. Elution, staring with pure methylene chloride with increasing methanol content, affords first 2-[1-(4-cyanophenyl)-3-(4-fluorophenyl)propyl]tetrazole which $^1$H NMR spectra is as follows:

$^1$H NMR (base, CDCl$_3$): 2.47–2.61 (m, 3H), 2.88–3.01 (m, 1H), 5.93 (dd, 1H), 6.96–7.10 (m, 4H), 7.51 (d, 2H), 7.67 (d, 2H), 8.57 (s, 1H)

Further elution affords 1-[1-(4-cyanophenyl)3-(4-fluorophenyl)propyl]tetrazole which $^1$H NMR spectra is as follows:

$^1$H NMR (base, CDCl$_3$): 2.50–2.65 (m, 3H), 2.86–2.93 (m, 1H), 5.54 (dd, 1H), 6.98–7.26 (m, 4H), 7.44 (d, 2H), 7.71 (d, 2H), 8.54 (s, 1H)

EXAMPLE 12

5-[1-(4-cyanophenyl)-3-(4-fluorophenyl)-1-propenyl]thiazole a) 5-[1-(4-cyanophenyl)-3-(4-fluorophenyl)-1-hydroxypropyl]thiazole 5-bromothiazole (1.66 g, 10 mmol) is dissolved in diethyl ether. n-Butyllithium (4.85 ml, 2.5 M) is added very slowly under nitrogen atmosphere at −60° C. After stirring for 20 minutes at −60° C. (4-cyanophenyl)-2-(4-fluorophenyl)ethyl ketone (2.5 g, 10 mmol) is added in diethyl ether at the same temperature and the stirring is continued for another 2 hours. The reaction mixture is allowed to warm to room temperature after which it is decomposed with saturated ammonium chloride solution. The diethyl ether layer is separated and the solvent is evaporated. Water is added and the product is extracted into ethyl acetate. After drying and evaporation of the solvent the residue is mixed with ethanol and the black precipitate is filtered off. The ethanol is evaporated and the product is purified by flash chromatography (eluent: dichloromethane/methanol 46:1).

$^1$H NMR (base, CDCl$_3$): 2.33–2.40 (m, 1H), 2.52–2.67 (m, 2H), 2.68–2.83 (m, 1H), 6.96 (t, 2H), 7.061 (dd, 2H), 7.65 (AB quart, 4H), 7.73 (s, 1H), 8.73 (s, 1H)

b) 5-[1-(4-cyanophenyl)-3-(4-fluorophenyl)-1-propenyl]thiazole

5-[1-(4-cyanophenyl)-3-(4-fluorophenyl)-1-propenyl]thiazole is prepared according to the procedure of Example 3b from 5-[1-(4-cyanophenyl)-3-(4-fluorophenyl)-1-hydroxypropyl]thiazole. The product contains mainly of isomer a. The isomers are separated by flash chromatography (eluent: ethyl acetate/methanol 99:1).

$^1$H NMR (base, CDCl$_3$):

isomer a: 3.35 (d, 2H), 6.37 (t, 1H), 6.70 (t, 2H), 7.03 (dd, 2H), 7.33 (s, 1H), 7.43 (d, 2H), 7.77 (d, 2H), 8.67 (s, 1H)

isomer b: 3.60 (d, 2H), 6.41 (t, 1H), 7.01 (t, 2H), 7.14 (dd, 2H), 7.39 (d, 2H), 7.60 (d, 2H), 7.79 (s, 1H), 8.92 (s, 1H)

We claim:

1. A compound of formula:

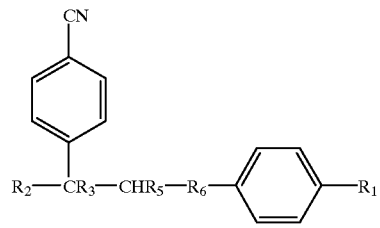

wherein $R_1$ is H, $CH_3$, $OCH_3$, $NO_2$, $NH_2$, CN, $CF_3$, $CHF_2$, $CH_2F$ or halogen; $R_2$ is 1-imidazolyl, $R_3$ is H or OH, $R_5$ is H or OH; $R_6$ is methylene, ethylene, —CHOH—, —CH$_2$—CHOH—, or —CHOH—CH$_2$—; or a stereoisomer thereof; or a non-toxic pharmaceutically acceptable acid addition salt thereof;

with the proviso that when $R_3$ and $R_5$ are H, $R_6$ cannot be methylene or ethylene.

2. A compound according to claim 1, wherein $R_3$ and $R_5$ combined form a bond, or $R_3$ is H and $R_5$ and $R_6$ combined form =O and $R_6$ is methylene or ethylene; or $R_3$ is H and $R_5$ and $R_6$ combined is =CH— or =CH=CH$_2$—; or $R_3$ and $R_5$ are H and $R_6$ is —CH=CH—, —C(=O)—, methylene or ethylene.

3. A compound according to claim 1 which is 1-[1-(4-cyanophenyl)4-(4-fluorophenyl)butyl]-1H-imidazole, a stereoisomer or a non-toxic pharmaceutically acceptable acid addition salt thereof.

4. A compound according to claim 1 which is 1-[1-(4-cyanophenyl)-4-(4-fluorophenyl)-2-hydroxybutyl]-1H-imidazole, a stereo isomer or a non-toxic pharmaceutically acceptable acid addition salt thereof.

5. A pharmaceutical composition comprising a compound as claimed in claim 1 and a pharmaceutically acceptable carrier.

6. A method of inhibiting aromatase comprising administering to a subject in which such inhibition is desired, an amount of a compound as claimed in claim 1 to produce the desired inhibition.

7. A compound according to claim 1, wherein $R_3$ is OH, $R_5$ is H, and $R_6$ is methylene or ethylene.

8. A compound according to claim 1, wherein $R_3$ and $R_5$ are H and $R_6$ is —CHOH—, —CH$_2$—CHOH—, or —CHOH—CH$_2$—.

9. A compound of formula:

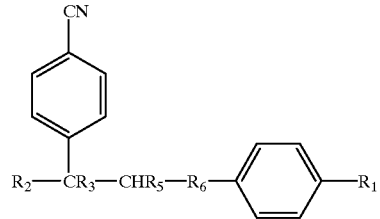

wherein $R_1$ is H, $CH_3$, $OCH_3$, $NO_2$, $NH_2$, $CF_3$, $CHF_2$, $CH_2F$, or halogen, $R_2$ is 1-imidazolyl, $R_3$ is H or OH, $R_5$ is H or OH; $R_6$ is methylene, ethylene, —CHOH—, —CH$_2$—CHOH—, or —CHOH—CH$_2$—; or a stereoisomer thereof; or a non-toxic pharmaceutically acceptable acid addition salt thereof;

with the proviso that when $R_3$ and $R_5$ are H, $R_6$ cannot be methylene or ethylene.

10. A compound of formula:

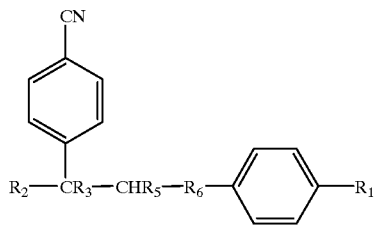

wherein $R_1$ is H, $CH_3$, $OCH_3$, $NO_2$, $NH_2$, CN, $CF_3$, $CHF_2$, $CH_2F$, or halogen, $R_2$ is 1-imidazolyl, $R_3$ is H or OH, $R_5$ is H or OH; $R_6$ is —CHOH—, —$CH_2$—CHOH—, or —CHOH—$CH_2$—; or a stereoisomer thereof; or a non-toxic pharmaceutically acceptable acid addition salt thereof;

with the proviso that when $R_3$ and $R_5$ are H, $R_6$ cannot be methylene or ethylene.

* * * * *

UNITED STATES PATENT AND TRADEMARK OFFICE
CERTIFICATE OF CORRECTION

PATENT NO.: 5,962,495

DATED: October 5, 1999

INVENTOR(S): Arto J. KARJALAINEN et al.

It is certified that an error appears in the above-identified patent and that said Letters Patent is hereby corrected as shown below:

Claim 3, col. 16, line 30, "cyanophenyl)4" should read --cyanophenyl)-4--.

Claim 4, col. 16, line 35, "stereo isomer" should read --stereoisomer--.

Signed and Sealed this

Twentieth Day of June, 2000

*Attest:*

Q. TODD DICKINSON

*Attesting Officer*         *Director of Patents and Trademarks*